United States Patent
Soubeyrat et al.

(10) Patent No.: US 9,538,939 B2
(45) Date of Patent: Jan. 10, 2017

(54) SYSTEM FOR ANALYZING A USER'S STRIDES

(75) Inventors: Cyrille Soubeyrat, Reaumont (FR); Anne Frassati, Voreppe (FR)

(73) Assignee: Movea, Grenoble (FR)

(*) Notice: Subject to any disclaimer, the term of this patent is extended or adjusted under 35 U.S.C. 154(b) by 341 days.

(21) Appl. No.: 13/643,061

(22) PCT Filed: Apr. 8, 2011

(86) PCT No.: PCT/EP2011/055573
§ 371 (c)(1),
(2), (4) Date: Oct. 23, 2012

(87) PCT Pub. No.: WO2011/131497
PCT Pub. Date: Oct. 27, 2011

(65) Prior Publication Data
US 2013/0041291 A1 Feb. 14, 2013

(30) Foreign Application Priority Data

Apr. 23, 2010 (FR) .................................... 10 53092

(51) Int. Cl.
*A61B 5/11* (2006.01)
*A61B 5/103* (2006.01)
*A61B 5/00* (2006.01)

(52) U.S. Cl.
CPC ............ *A61B 5/1038* (2013.01); *A61B 5/112* (2013.01); *A61B 5/1112* (2013.01);
(Continued)

(58) Field of Classification Search
CPC ... A61B 5/6829; A61B 5/1122; A61B 5/1112; A61B 5/1038; A61B 2503/10; A61B 5/112
(Continued)

(56) References Cited

U.S. PATENT DOCUMENTS 6,122,960 A * 9/2000 Hutchings ............... A63B 24/00
73/493
6,786,877 B2 * 9/2004 Foxlin .......................... 600/587
(Continued)

FOREIGN PATENT DOCUMENTS

EP  1 985 233 A1  10/2008
FR  2 860 700 A1  4/2005
(Continued)

OTHER PUBLICATIONS

International Search Report and Written Opinion issued in corresponding International Application No. PCT/EP2011/055573, dated Jun. 17, 2011.

*Primary Examiner* — Adam J Eiseman
*Assistant Examiner* — Patrick Fernandes
(74) *Attorney, Agent, or Firm* — Stroock & Stroock & Lavan LLP

(57) ABSTRACT

A system for analyzing a user's strides has a first sensor assembly (EC1) furnished within a housing, with a triaxial magnetometer (3M) fixed to the housing (BT), which is associated with a moving frame (LF). First fixing means (MF1) fixes the first sensor assembly (EC1) to a leg segment of the user. Processing means (MT) calculates the angle of yaw ($Yaw_{GF}$) and/or of pitch ($Pitch_{GF}$) and/or of roll ($Roll_{GF}$) of the first sensor assembly (EC1), and calculates the corresponding angular temporal variation or variations $$\left(\frac{dYaw_{GF}}{dt}, \frac{dPitch_{GF}}{dt}, \frac{dRoll_{GF}}{dt}\right),$$

in a fixed global frame (GF) relative to the terrestrial frame, on the basis of the measurements of the triaxial magnetometer (3M) delivered in the moving frame (LF).

12 Claims, 5 Drawing Sheets

(52) U.S. Cl.
CPC ........... *A61B 5/1122* (2013.01); *A61B 5/6829* (2013.01); *A61B 2503/10* (2013.01)

(58) Field of Classification Search
USPC ....................................................... 600/587
See application file for complete search history.

(56) References Cited

U.S. PATENT DOCUMENTS

| | | | |
|---|---|---|---|
| 2007/0123806 A1* | 5/2007 | Bouvier et al. | 600/595 |
| 2009/0079559 A1* | 3/2009 | Dishongh et al. | 340/539.13 |
| 2009/0198155 A1* | 8/2009 | Bonnet | 600/595 |
| 2011/0035172 A1* | 2/2011 | De Foras | 702/92 |

FOREIGN PATENT DOCUMENTS

| | | | |
|---|---|---|---|
| FR | 2 926 971 A1 | 8/2009 | |
| FR | 2 930 335 A1 | 10/2009 | |

\* cited by examiner

SYSTEM FOR ANALYZING A USER'S STRIDES

FIELD OF THE INVENTION

The invention pertains to a system for analyzing a user's strides.

CROSS-REFERENCE TO RELATED APPLICATIONS

This application is the National Stage of International Application No. PCT/EP2011/055573, filed on Apr. 8, 2011, which claims the benefit of French Patent Application No. 1053092, filed on Apr. 23, 2010, the contents of both of which are incorporated herein by reference.

BACKGROUND

Background of the Invention

Generally, the invention is related to the fields of motion capture, and the geolocation of moving individuals. Motion capture relates to general-public applications such as leisure applications (interactive games consoles, monitoring of sports movements, virtual reality or enhanced reality), applications for aiding the navigation of pedestrians (those used most at the present time being satellite navigation systems such as GPS), applications for aiding the mobility of vulnerable people or those temporarily debilitated by their environment (disabled people or those plunged into darkness), and fitness applications (pedometer, calculation of energy expenditure or of distance traveled). Motion capture also relates to medical applications (monitoring of elderly and/or dependent persons, analysis of gait for postural reeducation or aid to diagnosis), safety or rescue applications (locating of firemen inside a building on fire, operational monitoring of military personnel, or surveillance of prisoners), but also commercially directed applications (statistics on the trajectories followed by consumers in commercial centers or supermarkets, definition of archetypes of use, or proposal of topographically-dependent ("top( )-dependent") commercial services).

It is notably known to reconstruct the movement of an object or of a person furnished with an object comprising an emitter of signals that are recognized by a satellite navigation aid system, such as the GPS system, outdoors, and by a radiolocation system based on Ultra Large Band (ULB) or WiFi transmissions indoors.

In numerous geographical zones, external or internal, navigation based on satellite navigation aid or radiolocation systems turns out to be nonetheless very tricky, because of the obstruction of the radio signals that are required for the measurement of top( )-dependent metrics, for example in the case of unavailability of the signals emitted by one or more satellites of the navigation aid system that are required for the measurement of pseudo-distances. In practice, these situations of blocking or obstruction greatly degrade the precision of the location information, and sometimes even render the navigation aid service unavailable, as illustrated in the document "An evaluation of UWB localization under non line-of-sight (NLOS) propagation" (A. Maali, A. Ouldali, H. Mimoun, and G. Baudoin), published in Wireless Pervasive Computing, ISWPC, 3rd International Symposium, pages 379-382, May 2008. Generally, the realizations cited above exhibit cost, consumption, bulkiness, and/or infrastructure that are unsuitable, or indeed crippling, for general-public applications.

Other systems are aimed at devising a path starting from a given departure point, by using attitude sensors (accelerometer(s), magnetometer(s), gyrometer) which usually deliver inertial measurements. These measurements make it possible to ensure navigation by more or less precise and complicated means, such as described, for example in the documents "Inertial head-tracker sensor fusion by a complementary separate-bias kalman filter" (E. Foxlin) published in March 1996 in Virtual Reality Annual International Symposium, Proceedings of the IEEE 1996, pages 185-194; "Detection of spatio-temporal gait parameters by using wearable motion sensors" (K. Kogure, L. Seon-Woo, and K. Mase), published in 2005 in Engineering in Medicine and Biology Society, IEEE-EMBS 2005, 27th Annual International Conference of the, pages 6836-6839, 2005; "Pedestrian tracking with shoe-mounted inertial sensors" (E. Foxlin), published in November 2005 in Computer Graphics and Applications, IEEE, 25:38-46, November-December 2005; or "Integration of foot-mounted inertial sensors into a Bayesian location estimation framework" (P. Robertson, B. Krach), published in March 2008 in Positioning, Navigation and Communication, 2008, WPNC 2008, 5th Workshop on, pages 55-61. Such systems are of high cost and complexity, and often lack precision.

Video games consoles, such as the Wii, use optical and/or ultrasound sensors to determine the trajectory of a game control element. These systems are expensive and limited.

There also exist, as presented in the documents "Assessment of walking features from foot inertial sensing" (S. Scapellato, F. Cavallo, A. M. Sabatini, and C. Martelloni), published in March 2005 in Biomedical Engineering, IEEE Transactions on, pages 486-494, or "Multisensor approach to walking distance estimation with foot inertial sensing" (D. Alvarez, A. M Lopez, J. Rodriguez-Uria, J. C. Alvarez, and R. C. Gonzalez), published in August 2007 in Engineering in Medicine and Biology Society, 2007, EMBS 2007, 29th Annual International Conference of the IEEE, pages 5719-5722, systems which assume two accelerometers and a gyrometer that are disposed in the sagittal plane of a user and which make it possible to determine the attitude of this sensor in the plane. The acceleration is integrated on the axis of the foot. These systems have reduced cost, but exhibit other drawbacks. On the one hand, they assume that the sensors are placed perfectly in the sagittal plane, this being almost impossible to realize in practice by the user, and causes an estimation error related to the poor positioning of the sensor or sensors. Moreover, they assume that walking takes place in the sagittal plane, which may not be the case, during side-on walking, for example.

The document, "An innovative shoe-mounted pedestrian navigation system" (K. Fyfe, Gerard Lachapelle, R. Stirling, and J. Collin), published in April 2003 in Proc. European Navigation Conf. (GNSS), CD-ROM, Austrian Inst. of Navigation, discloses a system furnished with three accelerometers and with a fourth accelerometer to calculate the angle undergone by the sensor. This extra accelerometer is placed on the same mobile element, but some distance from the latter. The two sensors therefore see the same rotation and the same displacement. Such a structure makes it possible to estimate the rate of rotation of the mobile element, in rotation about a substantially constant direction, while dispensing with a gyrometer. This system has reduced cost due to the replacement of a mono-axis gyrometer by a pair of accelerometers with respect to the systems with gyrometers proposed by Alvarez et al and Scapellato et al. However, such a system exhibits the same drawbacks as the example cited hereinabove, since only the rotation about the axis orthogonal to the sagittal plane is taken into account. Furthermore, the estimation of the rotation by a pair of accelerometers, just like that carried out with the aid of a gyrometer, exhibits significant drifts. A heading is also determined with the aid of a magnetometer, for example when the foot is planted, thereby giving the direction of the foot and not the sought-after direction of the displacement.

French patent application FR 0857181 pertains to a device for determining a trajectory characteristic formed of successive positions of a triaxial accelerometer tied securely to a mobile element, between a first instant of immobility or of quasi-immobility and a second instant of immobility of quasi-immobility of the triaxial accelerometer, subsequent to said first instant, said device comprising, furthermore, a triaxial additional sensor for measuring a vector of a vector field which is substantially constant between said first and second instants of immobility, in a fixed global reference frame tied to the terrestrial reference frame. The additional sensor, for example a triaxial magnetometer, is tied securely to said mobile element fixed in the reference frame of the accelerometer, and the device comprises control means. Said control means comprises:

first means for determining said first and second instants of immobility of the triaxial accelerometer;

second means for determining a substantially invariant axis of rotation of the triaxial accelerometer between said first and second instants of immobility, and a plane orthogonal to said substantially invariant axis of rotation, in a moving reference frame tied to the accelerometer or to the additional sensor on the basis of the vectors delivered by the triaxial accelerometer, or on the basis of the vectors delivered by the additional sensor;

first means for calculating, at said successive instants, first orthogonal projections onto said plane of the vectors delivered by the triaxial accelerometer and of the vectors delivered by the additional sensor in said moving reference frame;

third means for determining, at said successive instants, the rotation for switching from said moving reference frame to said fixed global reference frame, on the basis of said first orthogonal projections of the vectors delivered by the additional sensor;

second means for calculating, at said successive instants, second orthogonal projections in said fixed global reference frame, of the first orthogonal projections, provided by said first calculation means, in said plane of the vectors delivered by the triaxial accelerometer;

third calculation means for subtracting from each second orthogonal projection in said fixed global reference frame the mean vector over said successive instants, so as to obtain the accelerations centered in said plane, devoid of the influence of the terrestrial gravity and of drifts of said device, in said fixed global reference frame; and fourth means for calculating a characteristic of the trajectory on the basis of the centered accelerations.

Such a device makes it possible to determine a planar trajectory of a triaxial accelerometer tied to a mobile element, notably a foot, for a stride, to thus reconstruct a trajectory of a set of successive strides. The mobile element may be another part of the human body, such as a hand, a part of an animal body, or a part of an artificial body such as a robot or a computer mouse.

Such a device makes it possible to obtain global information related to the displacement of the user in a sagittal plane. It does not make it possible to obtain information, in three dimensions, relating to the stride of a user, notably of a runner.

An aim of the invention is to alleviate these problems.

SUMMARY OF THE INVENTION

According to one aspect of the invention, there is proposed a system for analyzing a user's strides, comprising:

a first sensor assembly furnished with a housing, with a triaxial magnetometer fixed to said housing, and with a moving frame;

first fixing means adapted for fixing the first sensor assembly to a leg segment of the user; and processing means adapted for calculating the angle of yaw and/or of pitch and/or of roll of said sensor assembly, and for calculating the corresponding angular temporal variation or variations, in a fixed global frame tied to the terrestrial frame, on the basis of the measurements of said triaxial magnetometer, delivered in said moving frame.

Said processing means comprises:

first means for calculating the temporal variation of the angle of pitch of the first sensor assembly on the basis of the measurements of said triaxial magnetometer, delivered in said moving frame; and first means for determining an instant of start of a stride and an instant of end of said stride and phases of said stride, on the basis of said temporal variation of the angle of pitch of the first sensor assembly, provided by said first calculation means.

Such a system makes it possible to obtain information, in three dimensions, relating to the stride of a user.

Furthermore, the processing means may be internal or external to the housing, and when they are external, they may be embedded aboard a portable telephone or a laptop computer.

The term leg is understood to mean a complete lower limb. In a preferential manner, the leg segment to which the first sensor assembly EC1 may be fixed, is the instep or the metatarsus of the foot, or the tibia.

The first sensor assembly may be calibrated, if necessary, so that the moving frame is such that two axes form a vertical plane in a fixed global frame tied to the terrestrial frame.

In the subsequent description, the term frame may be associated with a reference frame associated with the frame.

It is thus possible, for example, to precisely determine the ground contact time (between the planting of the foot on the ground and the instant at which the foot will leave the ground) or the acceleration of the foot at the instant at which the foot will leave the ground, which are important characteristics of a runner's stride.

In one embodiment, said first sensor assembly is, furthermore, furnished with a triaxial accelerometer fixed to said housing, and said processing means comprises second means for determining values of parameters representative of a phase of said stride or of the complete stride, in three dimensions, in the fixed global frame.

Thus the precision of the system is improved, by obtaining information related to phases of the stride.

According to one embodiment, a stride comprising a phase of bearing of the foot to which the first sensor assembly is fixed, followed by a rear cycle phase in which said foot rises from the ground toward the user's back, and by a front cycle phase in which said foot is directed in front of the user, said second determining means comprising first means for estimating a frame associated with the first sensor assembly, for the stride and/or per phase of the stride, on the basis of a singular value decomposition, of the three-column matrix formed by vectors delivered by said triaxial magnetometer at successive instants, in the moving frame associated with the first sensor assembly.

The invention makes it possible to determine a variable frame associated with the first sensor assembly, for the whole of the stride and per phase of the stride, the phases of a stride are defined further on in the description.

The two vectors associated with the two largest singular values may form the principal plane of the stride.

In one embodiment, said processing means comprises second means for calculating orthogonal projections of the measurement vectors delivered by the triaxial accelerometer and by the triaxial magnetometer on the axes of the frame associated with the first sensor assembly over the stride.

Thus, it is possible to obtain the evolution of the axes of the magnetometer viewed from a frame presumed fixed during the stride, and to deduce therefrom the evolution of the angles describing the spatial attitude of the sensor assembly, therefore of the leg segment to which it is fixed, for example the foot.

According to one embodiment, the fixed global frame associated with the terrestrial frame is said orthogonal projection of the vectors delivered by the triaxial magnetometer in the frame associated with the first sensor assembly for the stride.

Indeed, this is possible since over a stride, the magnetic field remains substantially constant in a fixed global frame associated with the terrestrial frame.

In one embodiment, said second determining means comprises third means for determining the angles of pitch, of roll and of yaw of the first sensor assembly, on the basis of said orthogonal projection of the vectors delivered by the triaxial magnetometer in the frame associated with the first sensor assembly for the stride, and for determining the corresponding angular rates of pitch, of roll and of yaw.

By default, six degrees of freedom are thus determined, and then those which may be neglected are tested thereafter.

According to one embodiment, said second determining means comprises means for comparing said angular rates of pitch, roll and yaw with a threshold.

It is thus possible to test which degrees of freedom may be neglected.

In one embodiment, said second determining means comprises means for using the frame associated with the first sensor assembly for the phase in progress, when at least two of said absolute values of the three angular rates are greater than said threshold, so as to rectify the orientation by compensating for the trajectory deviations, due to the rotations, with respect to the global frame by using said frame associated with said first sensor assembly for the phase in progress in place of the frame associated with the first sensor assembly for the stride.

Rectification of orientation is understood as determining the trajectory in an appropriate frame, different from the frame calculated for the whole of the stride, because of the non-negligible angular rates which cause a deviation of the trajectory of the frame of the complete stride.

Thus, the reconstructed trajectory is composed of unit trajectories, for each phase of the stride, whose respective frames are suited to the number of degrees of freedom to be taken into account for each of the phases.

According to one embodiment, said first determining means are adapted for identifying characteristic instants of the user's stride by detecting local extrema of the temporal variation of the angle of pitch of the first sensor assembly.

It is thus easy to determine these characteristic instants of the stride.

In one embodiment, the second determining means comprises third calculation means for subtracting, from the vector corresponding to the orthogonal projection in the global frame of the measurement vector of the triaxial accelerometer delivered by the second calculation means, the mean vector over the stride of the orthogonal projection in the global frame of the measurement vector of the triaxial accelerometer delivered by the second calculation means, so as to obtain the centered vector of the accelerations in the global frame.

The obtaining of the accelerations centered in the global frame makes it possible to circumvent the influence of gravity.

According to one embodiment, the second determining means comprises fourth means for calculating a double temporal integration of said centered vector of the accelerations in the global frame delivered by said third calculation means, so as to obtain the trajectory of the first sensor assembly in said global frame, over the stride.

Thus, a three-dimensional characteristic of the user's stride is obtained for each phase of the stride.

Furthermore, the second determining means comprises means for correcting the drifts, by assuming that the foot of the user has an identical orientation at the start and end of stride, by rectification, so as to have identical vertical and transverse coordinates at the start and end of stride.

Thus, the trajectory is rectified, without resorting to calculations of angles between the global frame and the terrestrial frame.

The system can also comprise a second sensor assembly similar to the first sensor assembly, and second fixing means adapted for fixing the second sensor assembly to a segment of the other leg of the user.

The system can then, furthermore, comprise synchronization means for comparing the measurements performed by said sensor assembly or assemblies of one leg with respect to the other.

Thus, it is on the one hand possible to characterize the end of front cycle of one foot by measuring the contribution of the acceleration at the instant at which the other foot will leave the ground.

Moreover, the synchronous measurement of the two trajectories of the sensor assemblies coupled to the separate legs of the user makes it possible to determine the presence of temporal and spatial asymmetries of the runner's stride.

Furthermore, the system can comprise a third sensor assembly similar to the first sensor assembly, and third fixing means adapted for fixing the third sensor assembly at a position mid-height of the user.

Thus, a measurement of the trajectories of the two leg segments, notably of the two feet, performed in a manner synchronous with the measurement of the oscillation of the runner's center of mass in the sagittal plane makes it possible to determine the running phase to be modified so as to decrease the amplitude of said oscillation.

According to another aspect of the invention, there is also proposed a method for analyzing a user's strides, in which:

the temporary variation of the angle of pitch of a first sensor assembly, comprising a triaxial magnetometer, coupled to a leg segment of the user is calculated on the basis of the measurements of said triaxial magnetometer;

an instant of start of a stride and an instant of end of said stride and phases of said stride are determined on the basis of calculating the temporal variation of the angle of pitch of the first sensor assembly; and values of parameters representative of a phase of said stride, in three dimensions, are determined in a fixed global frame tied to the terrestrial frame.

BRIEF DESCRIPTION OF THE DRAWINGS

The invention will be better understood on studying a few embodiments described by way of wholly non-limiting examples and illustrated by the appended drawings in which.

DETAILED DESCRIPTION

In all figures, the elements having the same references are similar. In the present description, a complex system is described, notably illustrated by FIG. 4, but the invention also covers a less complex realization comprising just the elements making it possible to calculate the angle of yaw and/or of pitch and/or of roll, as well as the corresponding angular temporal variation or variations, in a fixed global frame associated with the terrestrial frame, on the basis of the measurements of a triaxial magnetometer, delivered in a frame associated with the magnetometer. Indeed, the whole of the part of the system illustrated in FIG. 4, wherein the arrows between elements are represented dashed, is optional, to obtain the complex system, the remainder of the figure represents a less complex embodiment making it possible to determine the angle of yaw ($Yaw_{GF}$) and/or of pitch ($Pitch_{GF}$) and/or of roll ($Roll_{GF}$) of said first sensor assembly (EC1), and to calculate the corresponding angular temporal variation or variations $$\left( \frac{dYaw_{GF}}{dt}, \frac{dPitch_{GF}}{dt}, \frac{dRoll_{GF}}{dt} \right),$$

in a fixed global frame associated with the terrestrial frame, on the basis of the measurements of said triaxial magnetometer, delivered in said moving frame.

Figure 1A:
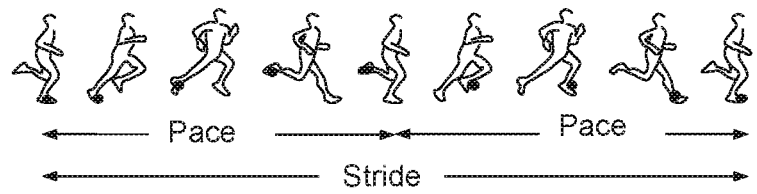
FIGS. 1a, 1b, and 1c schematically illustrate the decomposition of a stride, according to one aspect of the invention.

As illustrated in FIG. 1a, a runner's stride is decomposed into two successive paces (planting of the left foot and of the right foot). A stride is a running phase which occurs between two successive ground contacts of one and the same foot.

Figure 1B:
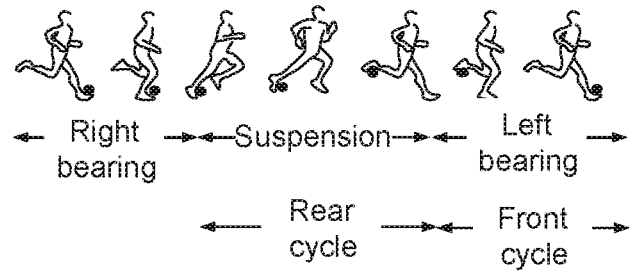

In FIG. 1b are represented the phases of a stride. The stride is decomposed into two distinct phases. The bearing phase during which one of the two feet is in contact with the ground, and the suspension phase during which both feet are in the air. During a flight phase of one foot (suspension and bearing of the other foot) is itself divided into two phases: a rear cycle phase during which the foot rises from the ground toward the runner's back, and a front cycle phase during which the foot is directed in the running direction, or in front of the user.

Figure 1C:
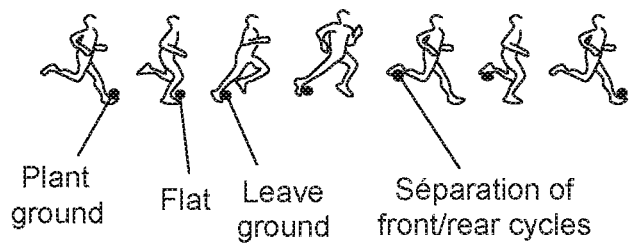

FIG. 1c represents the relevant events or instants characteristic of a stride. In the course of the stride, the trajectory of the foot is characterized by four notable characteristic instants:

maintaining of the foot flat or FF corresponding to maintaining the pelvis above the foot;

the instant at which the foot will leave the ground or TO for "Toe Off";

the instant at which the foot resumes toward the front or MSW for "Mid Swing" during the suspension phase; and planting of the foot on the ground or HS for "Heel Strike" corresponding to the start of the damping phase which is completed when the pelvis passes above the foot.

Figure 2:
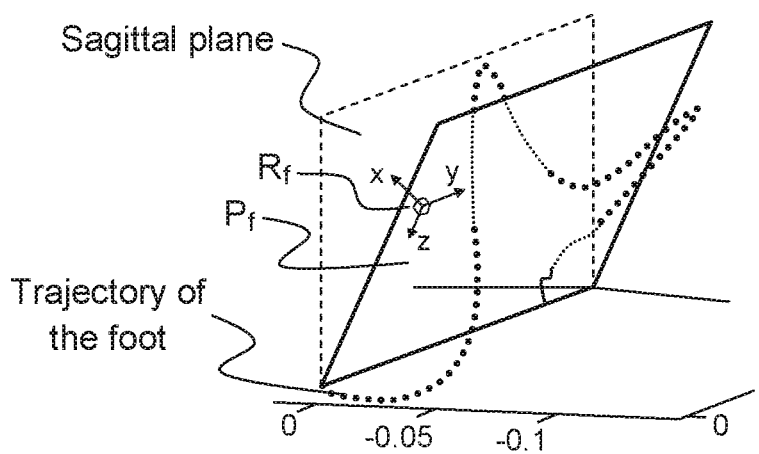
FIG. 2 schematically illustrates the displacement of a sensor assembly fixed to a user's foot, according to one aspect of the invention.

FIG. 2 illustrates the principal plane $P_f$ and the frame $R_f$ of the stride. In the course of the stride, the trajectory of the foot occurs in the vicinity of a plane $P_f$ being the principal plane of the stride. This plane exhibits an angle which is in general nonzero in relation to the sagittal plane, defined by the direction of the ground stride and the vertical. The frame of the stride is constructed on the basis of two axes of the principal plane $P_f$ of the stride and of a normal axis.

Figure 3A:
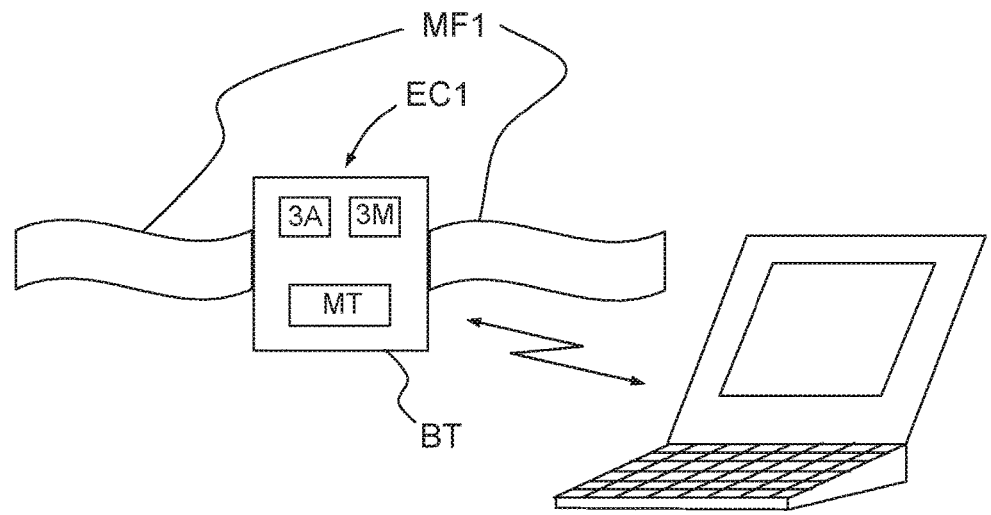
FIGS. 3a and 3b schematically illustrate a system according to one aspect of the invention.

FIG. 3a illustrates a system for analyzing a user's strides, comprising a first sensor assembly EC1 furnished with a housing BT, with a triaxial magnetometer 3M fixedly connected to the housing BT. The sensor assembly EC1 is furnished with a moving frame LF, such that two axes (y, z) form a vertical plane in a fixed global frame GF associated with the terrestrial frame. The system also comprises first fixing means MF1, for example elastic elements furnished with scratches, adapted for fixing the first sensor assembly EC1 to a segment of a leg of the user, for example a foot of the user. Furthermore, the first sensor assembly EC1 comprises an optional triaxial accelerometer 3A fixedly connected to the housing BT. Indeed, in the system described, in addition to the extraction of the angles and angular rates, the three-dimensional trajectory of the first sensor assembly EC1, and therefore of the leg segment to which it is fixedly connected, is determined.

The system comprises, furthermore, a processing module MT.

In this instance, the processing module MT is internal to the housing BT, and can transmit results to an outside terminal, such as a computer or a portable telephone, to display them. As a variant, a results display element could be integrated directly into the housing BT.

Figure 3B:
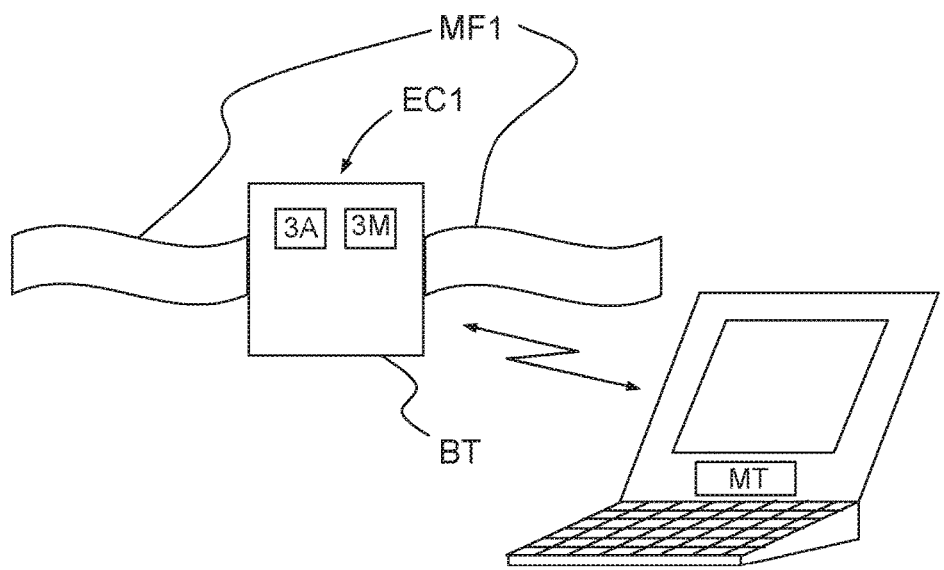

As a variant, such as illustrated in FIG. 3b, the processing module MT may be sited remotely in an outside terminal, such as a computer or a mobile telephone.

Figure 4:
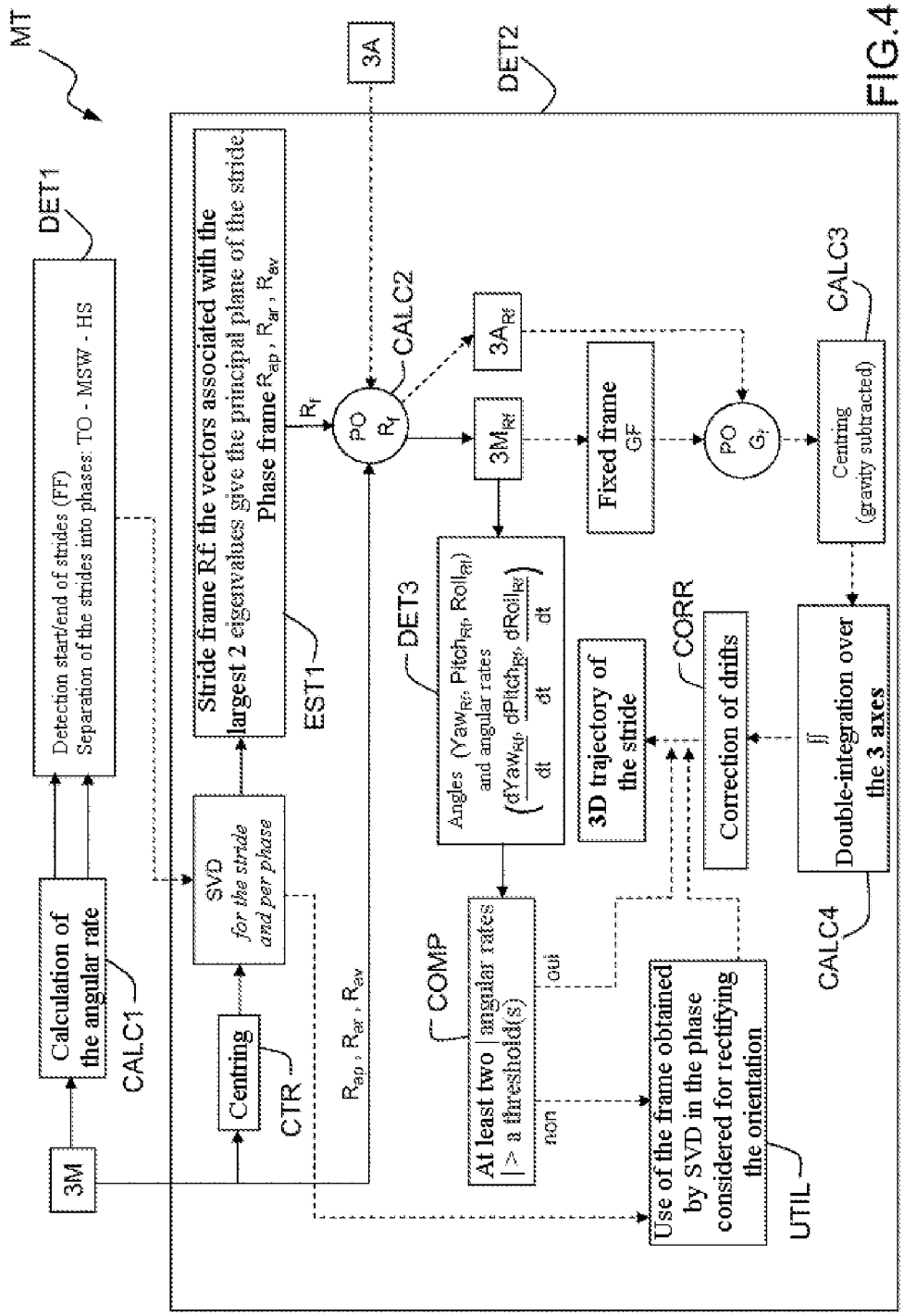
FIG. 4 illustrates in greater detail a processing module according to one aspect of the invention.

FIG. 4 illustrates in greater detail an embodiment of the processing module MT.

A first determining module DET1 makes it possible to determine an instant of start of a stride, an instant of end of said stride, and phases of said stride, on the basis of a temporal variation of the angle of pitch Pitch of the first sensor assembly EC1. A second determining module DET2 makes it possible to determine values of parameters representative of a phase of said stride, or of the complete stride, in three dimensions, in the fixed global frame GF.

The processing module MT comprises a first module CALC1 for calculating the temporal variation of the angle of pitch Pitch of the first sensor assembly EC1 in the moving frame LF on the basis of the measurements of the triaxial magnetometer 3M.

The second determining module DET2 comprises a first module EST1 for estimating a frame associated with the first sensor assembly EC1, for the stride $R_f$ and per phase $R_{ap}$, $R_{ar}$, $R_{av}$ of the stride, on the basis of a singular value decomposition or SVD, in said moving frame LF associated with the first sensor assembly EC1, of the three-column matrix formed by vectors delivered by the triaxial magnetometer 3M at successive instants in the moving frame LF.

The processing module MT comprises a second module CALC2 for calculating orthogonal projections PO of the measurement vectors delivered by the triaxial accelerometer 3A and by the triaxial magnetometer 3M onto the axes of the frame associated with the first sensor assembly over the stride $R_f$.

The fixed global frame GF associated with the terrestrial frame, is the orthogonal projection PO of the vectors delivered by the triaxial magnetometer 3M in the frame associated with the first sensor assembly EC1 for the stride $R_f$.

The second determining module DET2 comprises a third module DET3 for determining the angles of pitch $Pitch_{R_f}$, of roll $Roll_{R_f}$ and of yaw $Yaw_{R_f}$ of the first sensor assembly EC1, in the frame $R_f$ on the basis of the orthogonal projection PO of the vectors delivered by the triaxial magnetometer 3M in the frame LF associated with the first sensor assembly EC1 for the stride, and for determining the corresponding angular rates of pitch $$\frac{d Pitch_{R_f}}{dt},$$

of roll $$\frac{d Roll_{R_f}}{dt}$$

and of yaw $$\frac{d Yaw_{R_f}}{dt}.$$

The second determining module DET2 comprises means COMP for comparing the angular rates of pitch $$\frac{d Pitch_{R_f}}{dt},$$

of roll $$\frac{d Roll_{R_f}}{dt}$$

and of yaw $$\frac{d Yaw_{R_f}}{dt}$$

with a threshold S.

The second determining module DET2 comprises a module UTIL for using the frame $R_{ap}$, $R_{ar}$, $R_{av}$ associated with the first sensor assembly EC1 for the phase in progress, when at least two of said absolute values of the three angular rates are greater than said threshold S, to rectify the orientation, that is to say to reset the trajectory during the phase in progress of the stride, by using the frame $R_{ap}$, $R_{ar}$, or $R_{av}$ associated with the sensor assembly EC1 for the phase in progress in place of the frame $R_f$ associated with the first sensor assembly EC1 for the whole of the stride.

The first determining module DET1 is adapted for identifying characteristic instants HS, FF, TO, MSW of the user's stride by detecting local extrema of the temporal variation $$\frac{d Pitch}{dt}$$

of the angle or pitch Pitch in the frame associated with the first sensor assembly EC1.

Furthermore, the separation in phases by the first sensor assembly EC1 makes it possible to distinguish the stride moments during which the three-dimensional trajectory may theoretically be estimated, from the moments at which the overly large number of degrees of freedom prevents this (these numbers are obtained by extraction of the angular rates).

The bearing phase goes from the planting of the foot on the ground HS to the instant at which the foot will leave the ground TO: the number of majority degrees of freedom is two, since the roll Roll and the pitch Pitch, the accelerations and the yaw Yaw are negligible therein.

The rear cycle phase goes from the instant at which the foot will leave the ground TO to the instant separating the rear cycle from the front cycle MSW: the number of degrees of freedom is generally six, since the three accelerations and the three angles are not negligible.

The front cycle phase goes from the instant separating the rear cycle from the front cycle MSW to the planting of the foot on the ground HS: the roll Roll and the pitch Yaw are negligible therein, therefore it is four majority degrees of freedom.

The advantage of knowing this number of degrees of freedom is the ability to validate or otherwise the reconstructed trajectory obtained. In the bearing phase and front cycle phase, the fact of having fewer than five degrees of freedom makes it possible to reconstruct the trajectory in three dimensions. In the rear cycle phase, the number of degrees of freedom generally being six, a more thorough estimation of the parameters may be implemented so as to have the best possible estimation of the trajectory in three dimensions in the course of this phase.

Cutting up the stride makes it possible to process the signals separately, and it is also possible to calculate a different frame of the stride $R_f$ for each of the phases. There can thus be three singular value decompositions SVD performed instead of one, and the projections may be done phase by phase. Indeed, in the ground bearing phase, for example, the frame of the stride $R_f$ may be very different from the global frame GF estimated over an entire stride. Changing frame makes it possible to give more details in the orientation of the motion.

The second determining module DET2 comprises a third calculation module CALC3 for subtracting, from the vector corresponding to the orthogonal projection PO in the global frame GF of the measurement vector of the triaxial accelerometer 3A delivered by the second calculation module CALC2, the mean vector over the stride of the orthogonal projection PO in the global frame GF of the measurement vector of the triaxial accelerometer 3A delivered by the second calculation module CALC2, so as to obtain the centered vector of the accelerations in the global frame GF.

This centering makes it possible to obtain centered accelerations, i.e. devoid of the influence of terrestrial gravity in said fixed global reference frame.

The second determining module DET2 comprises fourth means CALC4 for calculating a double temporal integration of said centered vector of the accelerations in the global frame GF delivered by the third calculation module CALC3, so as to obtain the trajectory of the first sensor assembly EC1 in said global frame GF, over the stride.

Furthermore, a module CORR may correct drifts by assuming that the foot has an identical orientation at the start and end of stride. This correction module performs a deviation of the trajectory in such a way that the coordinates in height or altitude in the fixed global frame GF are the same at the start and at the end of a stride, and the perpendicular coordinates or those in the plane of the ground also.

The system can, furthermore, comprise a second sensor assembly EC2 similar to the first sensor assembly EC1, and a second fixing module MF2 adapted for fixing the second sensor assembly EC2 to the user's other foot. A synchronization module SYNC makes it possible to observe the events originating from the assemblies EC1 and EC2 with a common time base. It is thus possible, at any instant, to know the temporal discrepancy between an event measured by the first sensor assembly EC1 (the instant at which the left foot will leave the ground, for example) and another event measured by the second sensor assembly EC2 (the planting of the right foot on the ground, for example).

Furthermore, the system can comprise a third sensor assembly EC3 similar to the first sensor assembly EC1, and a third fixing module MF3 adapted for fixing the third sensor assembly EC3 at mid-height of the user, for example at the level of the abdomen.

Figure 5A:
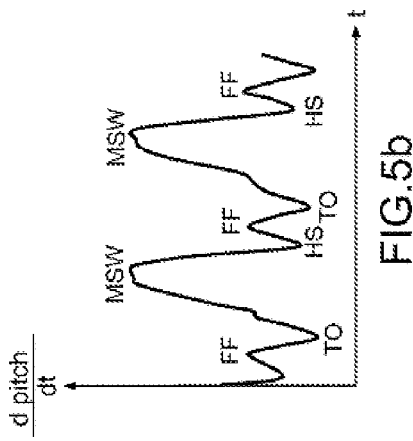
FIGS. 5a, 5b, 5c, and 5d illustrate elements of the processing module of FIG. 4.

FIG. 5a represents a foot furnished with a first sensor assembly EC1. The angular rate, or temporal variation of the angle of pitch Pitch of the first sensor assembly EC1, at the instant t, is given by $(Pitch(t_{n+1})-Pitch(t_n))$, with $Pitch(t)=\arctan(n_{AP}/m_{VT})$ where $m_{AP}$ and $m_{VT}$ are the measurements of the magnetometer 3M recorded in the principal plane $P_f$ of the stride (y and z directions).

Figure 5B:
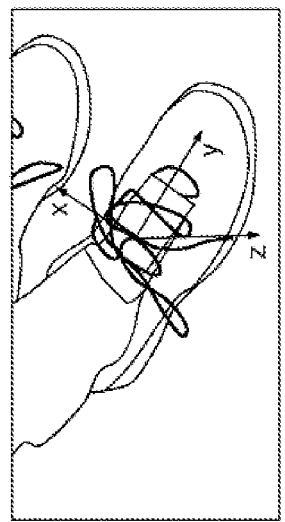

FIG. 5b represents the detection, by the first detection module DET1, of the characteristic instants HS, FF, TO, MSW of the stride. At the start of the pace FF, the acceleration is assumed zero. The various characteristic instants cited above HS, FF, TO, and MSW of the stride are detected at the local extrema. This type of detection is close to the scheme described in patent application FR 2926971.

It is possible to determine the principal axes of the motion, for example by using singular value decomposition (SVD). The calculation steps can include:
  a step of autocorrelation of the three components of the triaxial magnetometer 3M so as to obtain the covariance matrix, with three rows and three columns, of the signals of the magnetometer 3M;
  a step of decomposing the covariance matrix into eigenelements, each eigenvalue measuring the share of variance according to the associated eigenvector; and
  a step of principal component analysis, in which the data are projected onto each of the axes defined by the eigenvectors.

The plane $[\vec{u}_1, \vec{u}_2]$ of the trajectory is determined on the basis of the vectors delivered by the triaxial magnetometer 3M. The plane $[\vec{u}_1, \vec{u}_2]$ corresponds to the plane containing at the maximum of the measurements, considered to be points or vectors in a three-dimensional space by considering the measurements transmitted for each axis of the triaxial magnetometer, and the axis delineated by the vector $\vec{u}_3$ is the axis on which the projection of the measurements varies the least. The vector $\vec{u}_3$ is the vector normal to the plane of the trajectory $[\vec{u}_1, \vec{u}_2]$, but also the axis of rotation of the first sensor assembly EC1.

To determine these three vectors $\vec{u}_1, \vec{u}_2, \vec{u}_3$, we form a matrix $A^{LF}$ with n+1 rows, n+1 being the number of samples taken between $t_0$ and $t_n$ inclusive, and with 3 columns corresponding to the three measurements of the three axes x, y, z of the first sensor assembly EC1. We have:

$$A^{LF}(t_0, \ldots, t_n) = \begin{bmatrix} A_x^{LF}(t_0) & A_y^{LF}(t_0) & A_z^{LF}(t_0) \\ \ldots & \ldots & \ldots \\ A_x^{LF}(t_n) & A_y^{LF}(t_n) & A_z^{LF}(t_n) \end{bmatrix}$$

The measurements making it possible to form the matrix $A^{LF}$ may be the measurements of the triaxial magnetometer 3M or of the triaxial accelerometer 3A.

As a variant, it is possible to take just a subset of the samples at the successive instants $t_0, t_1, \ldots t_n$.

The three vectors $\vec{u}_1, \vec{u}_2, \vec{u}_3$, are determined on the basis of the matrix $ALF=(=A^{LF}(t_0, \ldots, t_n))$, by singular value decomposition SVD of the matrix $A^{LF}$: $A^{LF}=USV$. V is a matrix with three rows and three columns, each column of which corresponds to one of the three vectors $\vec{u}_1, \vec{u}_2, \vec{u}_3$. The matrix S contains the three singular values $s_1, s_2, s_3$. These three singular values $s_1, s_2, s_3$, must be ranked in descending order. The vector $\vec{u}_3$ is the column of the matrix V corresponding to the smallest singular value. The other two columns give the coordinates of the vectors forming the principal plane $P_f$ of the stride $[\vec{u}_1, \vec{u}_2]$.

The third calculation module CALC3 subtracts gravity after having projected the acceleration measured into the fixed frame GF, so as to extract the inherent acceleration.

For these purposes, the data are centered. Indeed, the speed is assumed to be zero at each foot flat FF, i.e. at the start and at the end of each stride.

Now, $$v(t) = \int_0^t a(u)\,du + v(0)$$

therefore if T is the duration of the stride, $$v(T) = \int_0^T a(u)\,du + v(0) = 0.$$

Since $v(0)=v(T)=0$, and by discretizing the integral sum, we obtain:

$$\sum_{i=0}^{N} a(t_i) = 0 \Leftrightarrow \overline{a} = 0.$$

The global mean of the acceleration is therefore zero over a stride, and it therefore suffices to subtract its mean from each of the components projected onto the 3 axes of the fixed frame, the contribution of gravity being constant there.

The fourth calculation module CALC4 performs a double temporal integration of the centered vector of the accelerations in the global frame GF delivered by the third calculation module CALC3, so as to obtain the trajectory of the first sensor assembly EC1 in the global frame GF, over the stride.

The integration scheme used is an adapted Simpson scheme or rectangle schemes. The first integration makes it possible to pass from the acceleration to the speed sample by sample. The second integration gives the distance on the basis of the speed, in the 3 dimensions.

Now, this speed is assumed to be zero at the instant t=0 (FF), this never being the case in practice. It is desirable to add a tangential speed R.

$$\frac{d\,Pitch_{R_f}}{dt},$$

R being the distance between the sensor and the metatarsus of the foot (where the speed is actually zero when planted on the ground) and $$\frac{d\,Pitch_{R_f}}{dt} = \left(Pitch_{R_f}(t_{n+1}) - Pitch_{R_f}(t_n)\right),$$

the pitch rate $$\frac{d\,Pitch_{R_f}}{dt}$$

being that provided by the third determining module DET3.

Experimental data have made it possible to estimate R and the orientation of this speed in the frame of the first sensor assembly, so as to give sufficiently precise contributions to each of the three integration axes.

The module CORR for correcting the drifts, after integration, three trajectories are obtained independently, along the three axes of the fixed frame. Let x be the horizontal axis in the direction of the stride, Z the vertical axis and y the horizontal axis perpendicular to the stride plane. The assumption is made that the foot has the same orientation at the start and at the end of the stride, and therefore on the one hand the trajectory z=f(x), on the other hand y=f(x), are rectified by establishing y(T)=y(0) and z(T)=z(0).

Figure 5C:
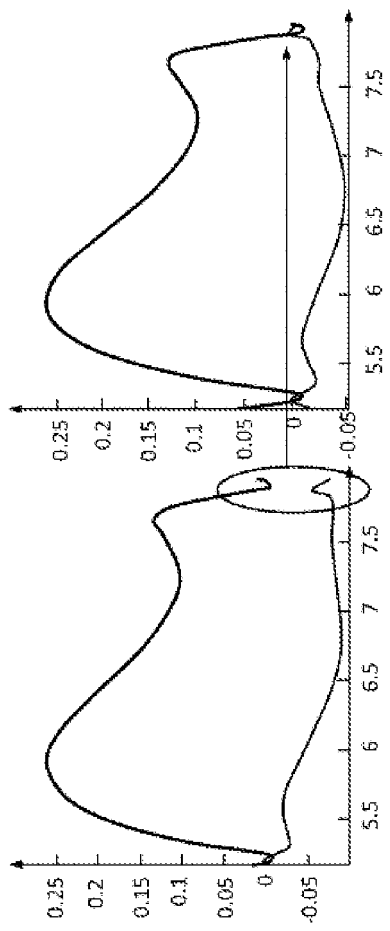

For example, as illustrated in FIG. 5c, are represented the curves z=f(x), and y=f(x): the latter, projected into the plane of the figure, is rectified so that the last point is common to the two trajectories. Stated otherwise, this is the trajectory reconstructed in a plane perpendicular to the plane given by the two principal directions of the trajectory $[\vec{u}_1, \vec{u}_2]$, with here a simple representation in two dimensions, which is rectified, i.e. wherein the coordinates at which the foot is planted at the end of the stride are assumed to be the same as those at the start of the stride, vertically and transversely (the foot must retouch the ground and it is assumed that the runner runs along a straight segment to facilitate the final representation of the trajectory).

The third module DET3 for determining the angles of pitch $Pitch_{R_f}$, of roll $Roll_{R_f}$ and of yaw $Yaw_{R_f}$ of the first sensor assembly EC1, on the basis of said orthogonal projection PO of the vectors delivered by the triaxial magnetometer 3M in the frame $R_f$ associated with the first sensor assembly EC1 for the stride, and for determining the corresponding angular rates of pitch $$\frac{d\,Pitch_{R_f}}{dt},$$

of roll $$\frac{d\,Roll_{R_f}}{dt}$$

and of yaw $$\frac{d\,Yaw_{R_f}}{dt}.$$

The measurements of the triaxial magnetometer 3M, projected onto the frame of the stride Rf, are used to calculate the three angles of the motion:
- the pitch $Pitch_{R_f}$: rotation about the axis perpendicular to the motion obtained by arctan ($B_{U2}/B_{U1}$);
- the roll $Roll_{R_f}$: rotation about the axis of the direction of the motion obtained by arctan ($B_{U1}/B_{U3}$); and
- the yaw $Yaw_{R_f}$: rotation about the vertical axis obtained by arctan ($B_{U3}/B_{U2}$);

with $B_{U1}/B_{U2}/B_{U3}$ the components of the magnetic field on the three axes of the stride frame Rf: mU1/mU2/mU3.

As a variant, these angles may be obtained differently, for example by obtaining the rotation matrix involving the three angles, on the basis of the projections $B_{U1}$, $B_{U2}$ and $B_{U3}$.

Knowing these three angles, it is possible to obtain the angular rates $$\frac{d\,Pitch_{R_f}}{dt}, \frac{d\,Roll_{R_f}}{dt} \text{ and } \frac{d\,Yaw_{R_f}}{dt}$$

instantaneously.

These values are generally small if the angles do not vary appreciably. For example, in the course of the front cycle phase, only the variation of the pitch Pitch is not negligible. The number of degrees of freedom in the motion is therefore less than or equal to four there. The reconstructed trajectory may be validated during this phase.

On the other hand, if two or three of these values are greater in absolute value than the threshold S, and if the accelerations along the three dimensions are greater, we have more than four degrees of freedom, and the validity of the trajectory is reduced.

In this case, it is possible to correct the reconstructed trajectory by refining the orientation of the stride by virtue of an SVD performed in this phase, which will give us the plane of the motion, different from the plane obtained over the whole of the stride.

Figure 5D:
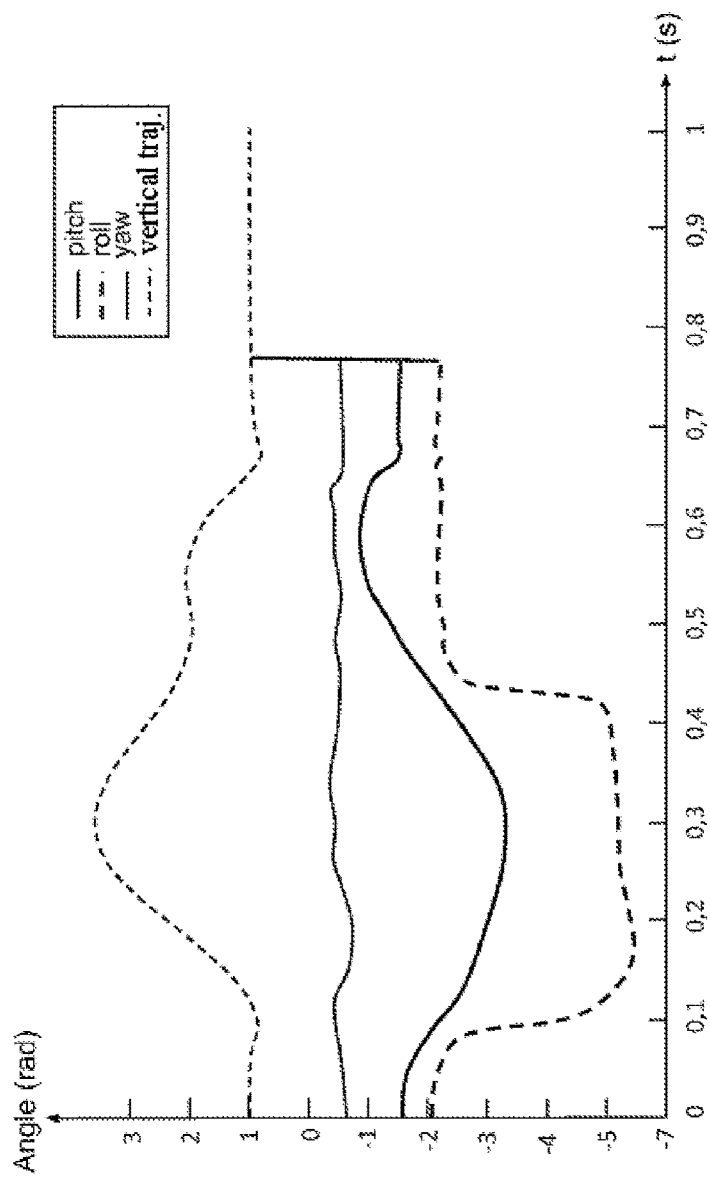

FIG. 5d represents the values of the three angles of pitch $\text{Pitch}_{R_f}$, of roll $\text{Roll}_{R_f}$ and of yaw $\text{Yaw}_{R_f}$ expressed in radians, as a function of time, expressed in seconds, in the course of a stride, as well as the vertical trajectory of this stride so as to visualize the evolutions of these angles as a function of the phases of the stride.

Such a system makes it possible to obtain information, in three dimensions, relating to the stride of a user, notably of a runner.

The invention claimed is:

1. A system for analyzing a user's strides, comprising:
a first sensor assembly having a housing, a triaxial magnetometer coupled to said housing, a triaxial accelerometer coupled to said housing, and having an associated moving frame;
first fixing means adapted for coupling the first sensor assembly to a limb segment of a user; and
a processor configured to calculate at least an angle of pitch of said first sensor assembly, and to calculate a corresponding angular temporal variation, in a fixed global frame associated with a terrestrial frame, utilizing measurements of said triaxial magnetometer delivered in said moving frame;
wherein the processor is further configured to:
determine an instant of start of a stride and an instant of end of said stride and phases of said stride, utilizing said temporal variation of the angle of pitch of the first sensor assembly;
calculate values of parameters representative of a phase of said stride or of the complete stride, in three dimensions in the fixed global frame, by calculating a stride frame associated with the first sensor assembly, for the complete stride or for each phase of the stride, utilizing vectors obtained from said triaxial magnetometer at successive instants in the moving frame associated with the first sensor assembly, the stride frame being a principal plane of the complete stride or for each phase of the stride, the principal plane being determined by the processor as orthogonal to an axis calculated as a spatial axis onto which projections of the vectors obtained from said triaxial magnetometer at successive instants vary the least; and
calculate orthogonal projections of measurement vectors obtained from the triaxial accelerometer and from the triaxial magnetometer on axes of the stride frame;
wherein the fixed global frame associated with the terrestrial frame is the orthogonal projection on the stride frame of the measurement vectors obtained from the triaxial magnetometer.

2. The system as claimed in claim 1, wherein calculating the values of the parameters further comprises determining angles of pitch, of roll and of yaw of the first sensor assembly, utilizing said orthogonal projection of the vectors delivered by the triaxial magnetometer in the stride frame calculating corresponding angular rates of pitch, of roll and of yaw.

3. The system as claimed in claim 2, wherein said calculating the values of the parameters further comprises comparing said angular rates of pitch, of roll and of yaw with a threshold.

4. The system as claimed in claim 3, wherein calculating the values of the parameters further comprises using a frame associated with the first sensor assembly for a phase in progress, when at least two absolute values of the three angular rates are greater than said threshold, so as to rectify an orientation by compensating for trajectory deviations, due to rotations, with respect to the global frame by using said frame associated with said first sensor assembly for the phase in progress in place of the stride frame.

5. The system as claimed in claim 1, wherein determining the instant of start of the stride and the instant of end of the stride and the phases of the stride further comprises identifying characteristic instants of the user's stride by detecting local extrema of a temporal variation of the angle of pitch of the first sensor assembly.

6. The system as claimed in claim 1, wherein calculating the values of the parameters further comprises subtracting, from a vector corresponding to an orthogonal projection in the global frame of the measurement vector of the triaxial accelerometer, a mean vector over the stride of the orthogonal projection in the global frame of the measurement vector of the triaxial accelerometer, so as to obtain a centered vector of accelerations in the global frame.

7. The system as claimed in claim 6, wherein calculating the values of the parameters further comprises calculating a double temporal integration of said centered vector of the accelerations in the global frame, so as to obtain a trajectory of the first sensor assembly in said global frame, over the stride.

8. The system as claimed in claim 1, wherein calculating the values of the parameters further comprises correcting drifts, by assuming that the user has an identical orientation at the start and at the end of the stride, by rectification, so as to have identical vertical and transverse coordinates at the start and at the end of the stride.

9. The system as claimed in claim 1, further comprising a second sensor assembly similar to the first sensor assembly, and second fixing means adapted for coupling the second sensor assembly to a segment of another limb of the user.

10. The system as claimed in claim 9, wherein the processor is further configured to compare the measurements performed by said sensor assembly or assemblies of the limb with respect to the other limb.

11. The system as claimed in claim 10, further comprising a third sensor assembly similar to the first sensor assembly, and third fixing means adapted for coupling the third sensor assembly at a mid-height of the user.

12. A method for analyzing a user's strides, in which:
a temporary variation of an angle of pitch of a first sensor assembly, comprising a triaxial magnetometer coupled to a limb segment of the user and a triaxial accelerometer coupled to said limb segment, is calculated utilizing measurements of said first sensor assembly;
wherein:
an instant of start of a stride and an instant of end of said stride and phases of said stride are determined by calculating a temporal variation of the angle of pitch of the first sensor assembly; and
values of parameters representative of a phase of said stride or of a complete stride, in three dimensions, are calculated in a fixed global frame associated with a terrestrial frame, by calculating a stride frame associated with the first sensor assembly based on vectors obtained from said triaxial magnetometer at successive instants, in a moving frame associated with the first sensor assembly, in which the stride frame is a principal plane of the complete stride or for each phase of the stride, the principal plane being determined as orthogonal to an axis calculated as a spatial axis onto which projections of the vectors obtained from said triaxial magnetometer at successive instants vary the least; and orthogonal projections of measurement vectors obtained from the triaxial accelerometer and from the triaxial magnetometer on axes of the stride frame associated with the first sensor assembly for the stride or per phase of the stride are calculated;

wherein the fixed global frame associated with the terrestrial frame is said orthogonal projection of the measurement vectors obtained from the triaxial magnetometer in the stride frame.

\* \* \* \* \*